(12) United States Patent
Sehgal

(10) Patent No.: US 8,927,203 B2
(45) Date of Patent: *Jan. 6, 2015

(54) PLATELET PRESERVATION PACKAGE COMPRISING A SHORT TO ULTRA-SHORT ACTING ANTIPLATELET AGENT AND ANTICOAGULANT

(75) Inventor: Lakshman R. Sehgal, Dana Point, CA (US)

(73) Assignee: Biovec Transfusion, LLC, Chicago, IL (US)

( * ) Notice: Subject to any disclaimer, the term of this patent is extended or adjusted under 35 U.S.C. 154(b) by 503 days.

This patent is subject to a terminal disclaimer.

(21) Appl. No.: 13/278,553

(22) Filed: Oct. 21, 2011

(65) Prior Publication Data

US 2012/0058558 A1 Mar. 8, 2012

Related U.S. Application Data

(60) Continuation of application No. 12/109,784, filed on Apr. 25, 2008, now Pat. No. 8,129,103, which is a division of application No. 11/330,132, filed on Jan. 12, 2006, now Pat. No. 7,964,338.

(60) Provisional application No. 60/643,107, filed on Jan. 12, 2005.

(51) Int. Cl.
*A01N 1/02* (2006.01)

(52) U.S. Cl.
CPC ............. *A01N 1/0215* (2013.01); *A01N 1/02* (2013.01); *A01N 1/0226* (2013.01)
USPC .................................................. 435/2

(58) Field of Classification Search
CPC .................................................. A01N 1/0226
See application file for complete search history.

(56) References Cited

U.S. PATENT DOCUMENTS

| | | | |
|---|---|---|---|
| 4,455,299 A | 6/1984 | Grode | |
| 4,800,016 A | 1/1989 | Yang | |
| 5,256,559 A * | 10/1993 | Maraganore et al. | 424/153.1 |
| 5,798,238 A | 8/1998 | Goodrich, Jr. et al. | |
| 5,801,063 A | 9/1998 | Grandics et al. | |
| 5,858,238 A | 1/1999 | Mcrea et al. | |
| 5,869,701 A | 2/1999 | Park et al. | |
| 5,919,614 A | 7/1999 | Livesey et al. | |
| 5,955,256 A | 9/1999 | Sowemimo-Coker et al. | |
| 5,981,163 A | 11/1999 | Horowitz et al. | |
| 6,030,767 A | 2/2000 | Wagner et al. | |
| 6,087,141 A | 7/2000 | Margolis-Nunno et al. | |
| 6,106,773 A | 8/2000 | Miekka et al. | |
| 6,733,471 B1 | 5/2004 | Ericson et al. | |
| 6,833,236 B1 | 12/2004 | Stienstra | |
| 7,964,338 B2 * | 6/2011 | Sehgal et al. | 435/2 |
| 8,129,104 B2 * | 3/2012 | Sehgal et al. | 435/2 |
| 8,142,992 B2 * | 3/2012 | Sehgal et al. | 435/2 |
| 8,329,389 B2 * | 12/2012 | Sehgal | 435/2 |
| 2001/0044584 A1 | 11/2001 | Kensey | |
| 2004/0223957 A1 | 11/2004 | Lucas et al. | |
| 2008/0138791 A1 | 6/2008 | Hoffmeister et al. | |
| 2010/0221697 A1 | 9/2010 | Sehgal | |

OTHER PUBLICATIONS

Bode et al., "Preservation of in vitro function of platelets stored in the presence of inhibitors of platelet activation and a specific inhibitor of thrombin" J. Lab. Clin. Med. 11 (1) : 118-124 (1988).*
Rosenkrantz et al., "Metabolic Disposition of Prostaglandin E-1 in Man", Biochimica et Biophysica Acta 750 (2) : 231-236 (1983), abstract only.*
Written Opinion of the International Search Authority (International Application No. PCT/US2010/037203, filed Jun. 3, 2010).
Wikipedia, "Eptifibatide", pp. 1-3.
Gao, C et al., "Eptifibatide-induced thrombocytopenia and thrombosis in humas require FcyRIIa and the integrin β3 cytoplasmic domain", The Journal of Clinical Investigation, Mar. 2009, vol. 11(3):504-511.
Gerbutavicius, R et al., "Differential effects of DX-9065a, argatroban, and synthetic pentasaccharide on tissue thromboplastin inhibition test and dilute Russell's viper venom test", U.S. National Library of Medicine, National Institute of Health. (Abstract).
Beilfu, A et al., "Differential Effects of Factor IIa Inhibitors on the Endogenous Thrombin Potential", Therapeutic Drug Monitoring, Dec. 2008, vol. 30(6):740-743. (Abstract).
American Heritage Stedman's Medical Dictionary 2002, definition of "cell culture", accessed Sep. 8, 2008.
Lowe, "Second-Generation Perfluorocarbon Emulsion Blood Substitutes", Art. Cells, Blood Subs. and Immob. Biotech. vol. 28, Issue 1, pp. 25-38 (2000).
Mousa, et al., "Antiplatelet and Antithrombotic Efficacy of DMP 728, a Novel Platelet GPIIb/IIIa Receptor Antagonist", Circulation, vol. 89, Issue 1, pp. 3-12 (1994).
Mousa, et al., "Comparison of the Effect of Different Platelet GPIIb/IIa Antagonists on the Dynamics of Platelet/Fibrin-Mediated Clot Strength Induced Using Thromboelastography", Thrombosis Research, vol. 104, pp. 49-56 (2001).
Warnholtz, et al., "Vasoactive Role of the αVβ3 iNtegrin in Rabbit Carotid Artery: Endothelium-Dependent and Independent Effects", American Heart Association, 71st Scientific Sessions (1998).
Supplementary European Search Report dated Oct. 27, 2011 of International Application No. 06718042.2.

(Continued)

*Primary Examiner* — Sandra Saucier
(74) *Attorney, Agent, or Firm* — Ping Wang; Andrews Kurth LLP

(57) ABSTRACT

The present invention relates to compositions and methods for storing platelets to preserve the function and freshness of the platelets. More particularly, the present invention relates to the use of a preservative composition having an antiplatelet agent, an anticoagulant, and an oxygen carrier, for maintaining the freshness of platelets. Additionally, the composition may also contain an ultra-short acting broad spectrum antimicrobial agents. The preservative composition may be used to store platelets in a liquid state, a frozen state, or a freeze-dried state.

13 Claims, 4 Drawing Sheets

(56) References Cited

OTHER PUBLICATIONS

Bode, A., et al., "Extended Storage of Platelets in an Artificial Medium with the Platelet Activation Inhibitors Prostaglandin E1 and Theophylline", Vox Sang, 1991, No. 60, pp. 105-112.

Leytin, V. et al., "Hemolink, an o-raffinose cross-linked haemoglobin-based oxygen carrier, does not affect activation and function of human platelets in whole blood in vitro", (Abstract).

Friesch, T. et al., "Artificial oxygen carriers", European Journal of Anaesthesiology, vol. 15, 1998, pp. 571-584.

Notification of Transmittal of the International Search Report and the Written Opinion of the International Searching Authority of International Application No. PCT/US2011/025432 dated Dec. 29, 2011.

Hirsh, J., et al., "New antithrombotic agents," The Lancet, vol. 353, pp. 1431-1436, Apr. 24, 1999.

Pinto, Donald J.P., et al., "Discovery of 1-[3-(Aminomethyl)phenyl]-N-[3-fluoro-2'-(methylsulfonyl)-[1,1'-biphenyl]-4-yl]-3-(trifluoromethyl)-1H-pyrazole-5-carboxamide (DPC423), a Highly Potent, Selective, and Orally Bioavailable Inhibitor of Blood Coagulation Factor Xa1," J. Med. Chem., vol. 44, pp. 566-578 (2001).

Pruitt, James R., et al., "Isoxazolines and Isoxazoles as Factor Xa Inhibitors," Bioorg. Med. Chem. Lett., vol. 10, pp. 685-689 (2000).

Quan, Mimi L., et al., "Design and Synthesis of Isoxazoline Derivatives as Factor Xa Inhibitors," J. Med. Chem., vol. 42, pp. 2752-2759 (1999).

Sato, K., et al., "Relationship between the antithrombotic effect of YM-75466, a novel factor Xa inhibitor, and coagulation parameters in rats," European Journal of Pharmacology, vol. 347, pp. 231-236 (1998).

Wong, P.C., et al., "Nonpeptide Factor Xa Inhibitors: 1. Studies with SF303 and SK5439, a New Class of Potent Antithrombotics," The Journal of Pharmacology and Experimental Therapeutics, vol. 292, No. 1, pp. 351-357 (2000).

Fareed, J., et al., "New antithrombotic drugs: A perspective," Current Opinion in Cardiovascular, Pulmonary & Renal Investigational Drugs, vol. 1, No. 1, pp. 40-55 (1999).

Herbert, J.M., et al., "DX 9065A, a Novel, Synthetic, Selective and Orally Active Inhibitor of Factor Xa: In Vitro and In Vivo Studies," The Journal of Pharmacology and Experimental Therapeutics, vol. 276, No. 3, pp. 1030-1038 (1996).

Nagahara, T., et al., "Design, Synthesis and Biological Activities of Orally Active Coagulation Factor Xa Inhibitors," Eur. J. Med. Chem., vol. 30 (Supplemental), pp. 140s-143s (1995).

Ewing, W.R., et al., "Progress in the design of inhibitors of coagulation factor Xa," Drugs of the Future, vol. 24, No. 7, pp. 771-787 (1999).

Al-Obeidi, F., et al., "Factor Xa inhibitors," Exp. Opin. Ther. Patents, vol. 9, No. 7, pp. 931-953 (1999).

Krishynamurti, C., et al., "Reduction of blood loss by infusion of human platelets in a rabbit kidney injury model," Transfusion, vol. 39, pp. 967-974 (Sep. 1999).

Mousa, S.A., et al., "Comparative in Vitro Efficacy of Different Platelet GPII/b/IIIa Antagonists on the Dynamic of Platelet / Fibrin-Mediated Clot Strength Induced by Different Mediators Using Thromboelastography: Differential Efficacy," Running title: "Platelet GPIIb/IIIa and Platelet/Fibrin Clot Retraction" (Paper submitted), pp. 1-21, Undated.

Abendschein, D.R., et al., "Effects of ZK-807834, a Novel Inhibitor of Factor Xa, on Arterial and Venous Thrombosis in Rabbits," J. Cardiovasc. Pharmacol., vol. 35, No. 5, pp. 796-805, retrieved Oct. 11, 2005, <http://gateway.ut.ovid.com.gw1/ovidweb/cgl>, May 2000.

Ostrem, J.A., et al., "Discovery of a Novel, Potent, and Specific Family of Factor Xa Inhibitors via Combinatorial Chemistry," Biochemistry, vol. 37, No. 4, pp. 1053-1059, 1998.

Bode, et al. "Extended Storage of Platelets in an Artificial Medium with the Platelets Activation Inhibitors Prostaglandin E1 and Theophylline", Vox Sang., vol. 60, pp. 105-112 (1991).

Uzan, "Antithrombotic Agents", Chapter 12, Emerging Drugs 3: 189-208 (1996).

Frietsch, et al. " Artificial Oxygen Carriers", European journal of Anesthesiology, vol. 15, pp. 571-584 (1998).

International Search Report (International Application No. PCT/US2010/037203, filed Jun. 3, 2010.

* cited by examiner

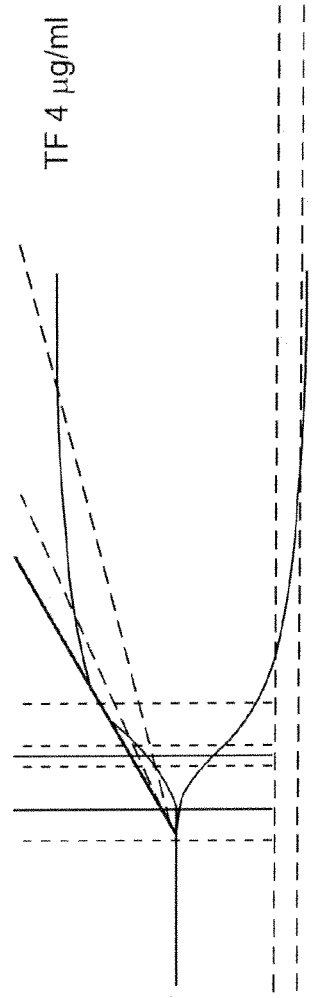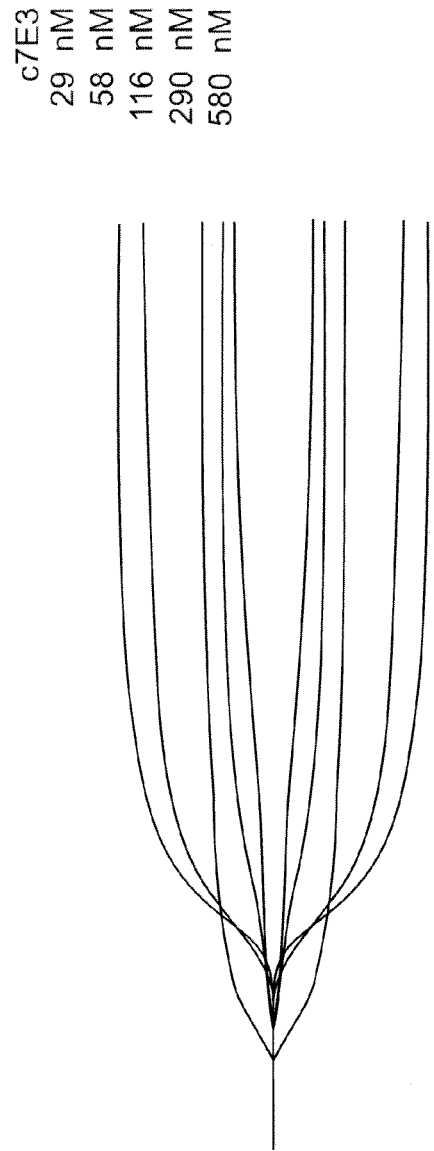
FIG. 2A
FIG. 2B

PLATELET PRESERVATION PACKAGE COMPRISING A SHORT TO ULTRA-SHORT ACTING ANTIPLATELET AGENT AND ANTICOAGULANT

This application is a continuation application of the U.S. patent application Ser. No. 12/109,784, filed Apr. 25, 2008, now U.S. Pat. No. 8,129,103, which is a divisional of U.S. patent application Ser. No. 11/330,132, filed Jan. 12, 2006, now U.S. Pat. No. 7,964,338, which claims priority from U.S. Provisional Application Ser. No. 60/643,107 filed Jan. 12, 2005. The entirety of all of the aforementioned applications is incorporated herein by reference.

FIELD

The present invention relates to a composition and method for extending the shelf-life of platelets. More particularly, the present invention relates to a preservative composition comprising an ultra-short acting antiplatelet agent and/or ultra-short acting anticoagulant and an oxygen carrier. The composition is particularly useful in extending life and maintaining the efficacy of platelets.

BACKGROUND

Whole blood contains the nutrients necessary to nourish tissues and organs in multi-cellular organisms. Arterial blood, or, blood carried in the arteries, is the blood in which oxygen and nutrients are transported to tissues. Venous blood, or blood carried in the veins, is the blood in which carbon dioxide and metabolic by-products are transported for excretion. These processes make it possible for nourishment to reach organs and tissues, and to sustain life in multi-cellular organisms.

Whole blood contains three components: (a) a fluid portion (plasma) with suspended elements, such as (b) red blood cells and white blood cells, and (c) platelets. The red blood cells are oxygen carriers and comprise an efficient oxygen carrier, called hemoglobin. Plasma is the liquid portion of the whole blood and contains nutrients, electrolytes (dissolved salts), gases, albumin, clotting factors, wastes, and hormones.

When blood vessels are damaged, cell fragments released from the bone marrow, called platelets, adhere to the walls of blood vessels and form clots to prevent blood loss. It is important to have adequate numbers of normally functioning platelets to maintain effective clotting, or coagulation, of the blood. Occasionally, when the body undergoes trauma, or when the platelets are unable to function properly, it is necessary to replace or transfer platelet components of blood into a patient. Most commonly, platelets are obtained from volunteer donors either as a component of a whole blood unit, or via plateletpheresis (withdrawing only platelets from a donor and re-infusing the remaining of the blood back into the donor). The platelets then are transferred to a patient as needed, a process referred to as "platelet transfusion".

Platelet transfusion is indicated under several different scenarios. For example, an acute blood loss, either during an operation or as a result of trauma, can cause the loss of a large amount of platelets in a short period of time. Platelet transfusion is necessary to restore a normal ability to control blood flow, or haemostasis. In a medical setting, an individual can develop a condition of decreased number of platelets, a condition known as thrombocytopenia. The condition can occur as a result of chemotherapy, and requires platelet transfusion to restore normal blood clotting.

Unlike red blood cells, which can be stored for forty-five (45) days, platelets can be stored for only five to seven days. The short storage term, or shelf-life, of the platelets severely limits the useful span for a platelet supply. A consequence of this short shelf-life is that platelets must be collected close to their time of use, which makes it extremely difficult to coordinate platelet collection and platelet supply.

One reason platelets have such short shelf-life is that platelets become activated during the process of collection. The activation process leads to externalization of platelet canalicular surfaces exposing receptor sites, such as GPIIb/IIIa. Phosphatidylserine residues on activated platelets tend to cause platelet aggregation, which results in cell death (i.e., apoptosis) upon re-infusion into patients. Thus, a platelet functional half-life is significantly reduced.

Another reason that platelets have a short shelf-life is that an inadequate oxygen supply alters the metabolic activity of the platelets. In an environment lacking a sufficient oxygen supply, the platelets undergo an anaerobic mechanism leading to accumulation of lactic acid. The increased concentration of lactic acid causes a drop in pH, and results in cell death. Although platelets can be stored in gas permeable bags using a shaker bath under a stream of air to help overcome this problem, such storage methods are costly and extremely inefficient and inadequate in meeting the oxygen requirements of the stored platelets.

Platelet sterility is difficult to maintain because platelets cannot be stored at low temperatures, for example 4° C. to 5° C. As previously mentioned, a low storage temperature for the platelets initiates an activation process within the platelets that leads to aggregation and cell death. Unfortunately, bacterial growth in the platelet medium at suitable storage temperatures, e.g., room temperature, can lead to an unacceptable occurrence of bacterial contamination in platelets used for transfusion. As a result, the Food and Drug Administration (FDA) limits the storage time of platelets to five (5) days, thereby safeguarding the transfusion supply from bacterial contamination.

Many sterilization methods have been suggested. Platelet compositions typically can be sterilized by radiation, chemical sterilization, or a combination thereof. For example, a method of inactivating viral and bacterial blood contaminants using a quinoline as a photosensitizer is disclosed in U.S. Pat. No. 5,798,238. Other classes of photosensitizers are, for example, psoralens, coumarins, or other polycyclic ring compounds, as disclosed in U.S. Pat. No. 5,869,701; quinolones, as disclosed in U.S. Pat. No. 5,955,256; free radical and reactive forms of oxygen, as disclosed in U.S. Pat. Nos. 5,981,163 and 6,087,141; and phenothiazin-5-ium dyes, as disclosed in U.S. Pat. No. 6,030,767. U.S. Pat. No. 6,106,773 discloses another method for disinfecting biological fluids, including platelets, by contacting the biological fluids with an iodinated matrix material.

These sterilization methods, however, do not extend storage life but on the contrary, appear to significantly decrease their functionality. To effectively extend the shelf life of platelets, not only are sterilization methods for preventing contamination of the platelets important, but it also would be beneficial to provide improved methods to protect the platelets during the sterilization. It would also be beneficial to provide a convenient, effective preservative solution for prolonging the shelf-life of the platelets, while maintaining the functionality and freshness of the platelets. In addition, it would be beneficial to provide a method or composition for storing platelets that requires less management of the surrounding platelet storage environment.

SUMMARY

One aspect of the present invention relates to a platelet preservation composition comprising (a) an antiplatelet agent, (b) an anticoagulant, and (c) an oxygen carrier. The preservative composition, when added to freshly collected platelets, permits an extended storage of platelets at ambient temperatures, and maintains blood clotting properties without affecting the half-life of the platelets in circulation after transfusion.

In one embodiment, the antiplatelet agent is capable of reversibly blocking platelet activation and/or aggregation by blocking sites on the platelet surface.

In another embodiment, the antiplatelet agent is selected from the group consisting of a compound that binds to, or associates with a GPIIb/IIIa receptor site, a non-steroidal anti-inflammatory drug (NSAID), a calcium channel blocker, $\alpha$-blocker, $\beta$-adrenergic blocker, and mixtures thereof.

In another embodiment, the anticoagulant is a compound that reversibly inhibits factor Xa, or factor IIa, or both.

In another embodiment, the anticoagulant is a short-to-ultrashort acting Xa inhibitor.

In another embodiment, the anticoagulant is a short-to-ultrashort acting IIa inhibitor.

In another embodiment, the oxygen carrier is a hemoglobin-based oxygen carrier.

In yet another embodiment, the oxygen carrier is selected from the group consisting of hemoglobin, ferroprotoporphyrin, perfluorochemicals, and mixtures thereof.

In yet another embodiment, each the hemoglobin-based oxygen carrier is substantially free of red cell membrane contaminants.

In another embodiment, the platelet preservation composition further comprises a short or ultra-short acting anti-microbial agent.

In another embodiment the platelet preservation composition can be used in a concentration range from about 0.001 to about 5 mg in any setting that requires the circulation of blood outside the body such as in patients undergoing open heart surgery, renal dialysis, plasmapheresis, and other procedures requiring platelet supplementation.

Another aspect of the invention relates to a preserved platelet composition comprising the platelet preservation composition described above and inactivated, functional platelets.

In one embodiment, the platelets in the preserved platelet composition are substantially free of red blood cells or other blood nutrients.

Another aspect of the present invention relates to a method of extending the shelf-life of platelets. The method comprises the steps of (a) admixing a preservative composition with inactivated, functional platelets and (b) store the preserved platelet in an oxygen-permeable container or an oxygen-impermeable container, wherein the preservative composition comprises a pharmaceutically acceptable antiplatelet agent, a pharmaceutically acceptable anticoagulant, and a pharmaceutically acceptable oxygen carrier.

In an embodiment, the inactivated, functional platelets are freshly collected platelets and are substantially free of red blood cells and other blood nutrients.

In another embodiment, the preservative composition further comprises a short-to-ultrashort acting broad spectrum anti-microbial agent.

BRIEF DESCRIPTION OF THE FIGURES

FIG. 2A shows the initiation of platelet/fibrin clot by tissue factor (TF) in human blood using thromboelastography (TEG). FIG. 2B shows the inhibition of platelet/fibrin clot induced by TF with different concentrations of c7E3 (antibody against platelet GPIIb/IIIa).

DETAILED DESCRIPTION OF THE INVENTION

Figure 1:
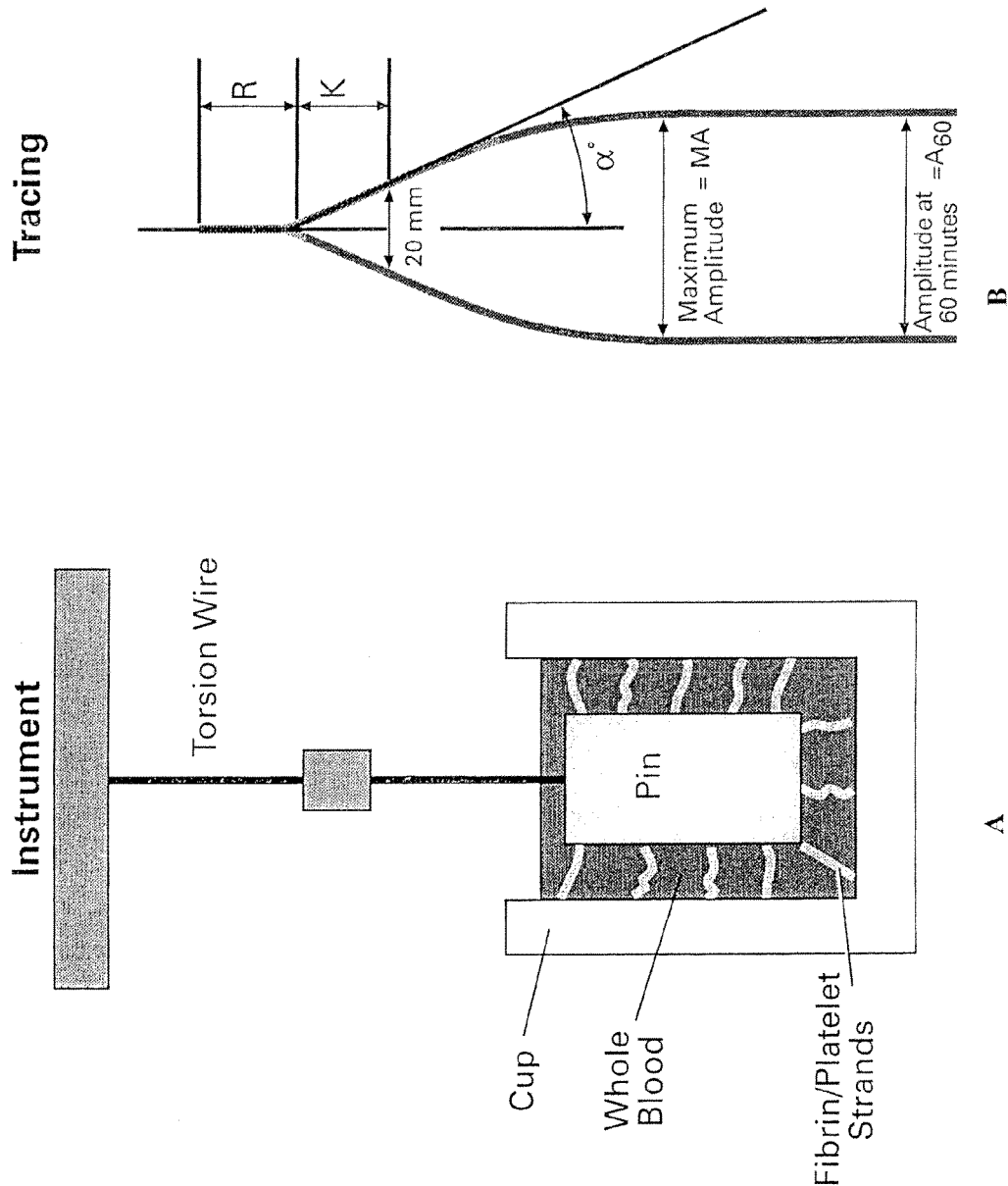
FIGS. 1A and 1B are the diagrams of TEG and tracing showing the initiation and completion phases of platelet-fibrin clot initiated by TF (25 ng) under shear in human whole blood (WB).

The following detailed description is presented to enable any person skilled in the art to make and use the invention. For purposes of explanation, specific nomenclature is set forth to provide a thorough understanding of the present invention. However, it will be apparent to one skilled in the art that these specific details are not required to practice the invention. Descriptions of specific applications are provided only as representative examples. Various modifications to the preferred embodiments will be readily apparent to one skilled in the art, and the general principles defined herein may be applied to other embodiments and applications without departing from the scope of the invention. The present invention is not intended to be limited to the embodiments shown, but is to be accorded the widest possible scope consistent with the principles and features disclosed herein.

One aspect of the present invention relates to a preservative composition that preserves the freshness of platelets. The preservative composition extends the shelf-life of donated platelets. The preservative composition comprises an antiplatelet agent, an anticoagulant, and an oxygen carrier.

The term "pharmaceutically acceptable" as used herein refers to a substance that complies with the regulations enforced by the FDA regarding the safety of use in a human or animal subject or a substance that has passed the FDA human safety trials. The term "pharmaceutically acceptable antiplatelet agent", for example, refers to an active agent that prevents, inhibits, or suppresses platelet adherence and/or aggregation, and comports with guidelines for pharmaceutical use as set forth by the FDA.

Any agent that reversibly impedes platelet activation and/or aggregation by blocking sites on the platelet surface can be used as the antiplatelet agent in the present invention. As used herein, the term "reversible" or "reversibly" refers to an act, such as binding or associating, that is capable of reverting back to an original condition prior to the act, for example the state of being unbound or disassociated, either with or without the assistance of an additional constituent.

As used herein, the term "effective amount" refers to a quantity that is capable of achieving an intended effect.

The temperature used in the present invention is from about −80° C. to 42° C. As used herein, the term "room temperature" or "ambient temperature" refers to a temperature in the range of 12° C. to 30° C.; the term "body temperature" refers to a temperature in the range of 35° C. to 42° C.; the term "refrigeration temperature" refers to a temperature in the range of 0° C. to 12° C.; and the term "freezing temperature" refers to a temperature below 0° C.

Generally, agents that can impede platelet activation and/or aggregation include, but are not limited to, heparin, heparin substitutes, prothrombopenic anticoagulants, platelet phosphodiesterase inhibitors, dextrans, and the like, or mixtures thereof Examples of heparin and heparin substitutes include, but are not limited to, heparin calcium, such as calciparin; heparin low-molecular weight, such as enoxaparin and lovenox; heparin sodium, such as heparin, lipo-hepin, liquaemin sodium, and panheprin; and heparin sodium dihydroergotamine mesylate. Suitable prothrombopenic anticoagulants are, for example, anisindione, dicumarol, warfarin sodium, and the like. More specific examples of phosphodiesterase inhibitors suitable for use in the invention include, but are not limited to, anagrelide, dipyridamole, pentoxifyllin, and theophylline. Examples of dextrans are, for example, dextran 70, such as HYSKON® (CooperSurgical, Inc., Shelton, Conn., U.S.A.) and MACRODEX® (Pharmalink, Inc., Upplands Vasby, Sweden), and dextran 75, such as GENTRAN® 75 (Baxter Healthcare Corporation, Deerfield, Ill., U.S.A.).

Antiplatelet agents can include, but are not limited to, active agents that bind GPIIb/IIIa sites in a reversible manner and non-steroidal anti-inflammatory drugs (NSAIDs). In a preferred composition, the active agents for binding to or associating with GPIIb/IIIa sites have a circulating half-life of inhibition of 4 hours or less. Examples of suitable antiplatelet agents for binding GPIIb/IIIa sites in a reversible manner are eptifibatide (INTEGRILIN®, Schering-Plough Corporation, Kenilworth, N.J., U.S.A.), orbofiban, xemilofiban, Lamifiban, tirofiban, abciximab, XJ757, DUP728, XR299, linear or novel cyclic RGD peptide analogs, cyclic peptides, peptidomimetics and non-peptide analogs conjugated to Nitric Oxide donor and the like, and mixtures thereof.

Non-steroidal anti-inflammatory drugs (NSAIDS) are commonly available, and typically are used for treating inflammation. Generally, NSAIDS can have a salicylate-like or non-salicylate structure. NSAIDS suitable for the invention can be salicylate-like or non-salicylate NSAIDS that bind reversibly and inhibit platelet aggregation in vitro, but are cleared rapidly, i.e. quickly eliminated from the body, when infused (typically, in less than about 2 hours). NSAIDS suitable for the invention include, but are not limited to, for example, salicylate-like NSAIDS, such as acetaminophen, carprofen, choline salicylate, magnesium salicylate, salicylamide, sodium salicylate, sodium thiosulfate, and the like, and mixtures thereof. Examples of non-salicylate NSAIDS include, but are not limited to, diclofenac sodium, diflunisal, etodolac, fenoprofen calcium, flurbiprofen, hydroxychloroquin, ibuprofen, indomethacin, ketoprofen, ketorolac tromethamine, meclofenamate sodium, mefenamic acid, nabumetone, naproxen, naproxen sodium, oxyphenbutazone, phenylbutazone, piroxicam, sulfinpyrazone, sulindac, tolmetin sodium dimethyl sulfoxide, and the like, and mixtures thereof.

In addition, any agent that inhibits chemical pathways within the platelets leading to reduction in platelet activation, is suitable for the invention. Typically, agents that inhibit chemical pathways leading to reduced platelet activation are calcium sequestering agents, such as calcium channel blockers, α-blockers, β-adrenergic blockers, and the like, and mixtures thereof. More specific examples of calcium sequestering agents include, but are not limited to, anticoagulant citrate dextrose solution, anticoagulant citrate dextrose solution modified, anticoagulant citrate phosphate dextrose solution, anticoagulant sodium citrate solution, anticoagulant citrate phosphate dextrose adenine solution, potassium oxalate, sodium citrate, sodium oxalate, amlodipine, bepridil hydrochloride, diltiazem hydrochloride, felodipine, isradipine, nicardipine hydrochloride, nifedipine, nimodipine, verapamil hydrochloride, doxazosin mesylate, phenoxybenzamine hydrochloride, phentolamine mesylate, prazosin hydrochloride, terazosin hydrochloride, tolazoline hydrochloride, acebutolol hydrochloride, atenolol, betaxolol hydrochloride, bisoprolol fumarate, carteolol hydrochloride, esmolol hydrochloride, indoramine hydrochloride, labetalol hydrochloride, levobunolol hydrochloride, metipranolol hydrochloride, metoprolol tartrate, nadolol, penbutolol sulfate, pindolol, propranolol hydrochloride, terazosin hydrochloride, timolol maleate, guanadrel sulfate, guanethidine monosulfate, metyrosine, reserpine, and the like, and mixtures thereof.

The antiplatelet agent can be used in conjunction with a pharmaceutically acceptable oxygen carrier. The oxygen carrier can be any suitable red blood cell substitute. Typically, the oxygen carrier is an acellular hemoglobin-based oxygen carrier substantially free of red cell membrane (stroma) contaminants. The term "pharmaceutically acceptable oxygen carrier" as used herein refers to a substance that has passed the FDA human safety trials at a hemoglobin dosage of 0.5 g/kg body weight or higher. An oxygen carrier suitable for the invention can be hemoglobin, ferroprotoporphyrin, perfluorochemicals (PFCs), and the like. The hemoglobin can be from human or any other suitable mammalian source. In a preferred embodiment, the preservative composition has a hemoglobin concentration from the range of 1 to 18 gm/dl and a methemoglobin concentration of less than about 5%. The hemoglobin based oxygen carrier will be chemically modified to mimic the oxygen loading and unloading characteristics of fresh red blood cells. Additionally, the chemical modification will enhance the buffering capacity of the preferred embodiment and preserve normal physiologic pH.

The amount of the antiplatelet agent present in the preservative composition depends on the type of antiplatelet agent. The amount of antiplatelet agent is sufficient to reversibly inhibit binding to a ligand or site on the platelet in a manner that is sufficient to inhibit platelet function, when bound. For GPIIb/IIIa inhibitors, suitable amounts in the preservative composition are about 0.5 mg to about 3 mg for 50 ml of acellular hemoglobin-based oxygen carrier substantially free of red cell membrane (stroma) contaminants. NSAIDs, for example, ibuprofen, are present in the preservative composition in an amount of about 20 mg to about 60 mg for each 50 ml of acellular hemoglobin-based oxygen carrier that is substantially free of red cell membrane contaminants.

The anticoagulants of the present invention include Xa inhibitors, IIa inhibitors, and mixtures thereof. Various direct Xa inhibitors were synthesized and advanced to clinical development (Phase I-II) for the prevention and treatment of venous thromboembolic disorders and certain settings of arterial thrombosis [Hirsh and Weitz, Lancet, 93:203-241, (1999); Nagahara et al., Drugs of the Future, 20: 564-566, (1995); Pinto et al., 44: 566-578, (2001); Pruitt et al., Biorg. Med. Chem. Lett., 10: 685-689, (2000); Quan et al., J. Med. Chem. 42: 2752-2759, (1999); Sato et al., Eur. J. Pharmacol., 347: 231-236, (1998); Wong et al, J. Pharmacol. Exp. Therapy, 292:351-357, (2000)]. A direct anti-IIa (thrombin) such as melagatran, the active form of pro-drug ximelagatran [Hirsh and Weitz, Lancet, 93:203-241, (1999); Fareed et al., Current Opinion in Cardiovascular, pulmonary and renal investigational drugs, 1:40-55, (1999)]. Additionally, a number of VIIa inhibitors and anti-tissue factors are in pre-clinical and early stage of clinical development. Formulation of zwitterionic short acting GPIIb/IIIa antagonists with small molecules direct Xa inhibitor, IIa inhibitor or mixed Xa and IIa inhibitors as defined by Mousa et al., Athero. Thromb. Vasc. Biol., 2000) would provide an optimal platelet preservation. Short to ultra-short acting GPIIb/IIIa antagonist might include eptifibatide, tirofiban, DUP728, abciximab (Reopro), lefradafiban, sibrafiban, orbofiban, xemilofiban, lotrafiban, XJ757, and XR299 (Class II). Short to ultra-short acting anticoagulant might include those direct Xa inhibitors, such as DX-9065a, RPR-120844, BX-807834 and SEL series Xa inhibitors, or direct IIa inhibitors, such as DUP714, hirulog, hirudin, and other short acting peptidomimetic or non-peptide Xa inhibitors, IIa inhibitors, or mixtures thereof. Some of these inhibitors are discussed in more details below.

DX-9065a is a synthetic, non-peptide, propanoic acid derivative, 571 Da, selective factor Xa inhibitor (Daiichi). It directly inhibits factor Xa in a competitive manner with an inhibition constant in the nanomolar range [Herbert et al., J. Pharmacol. Exp. Ther. 276:1030-1038 (1996); Nagahara et al., Eur. J. Med. Chem. 30 (suppl): 140s-143s (1995)].

As a non-peptide, synthetic factor Xa inhibitor, RPR-120844 (Rhone-Poulenc Rorer), is one of a series of novel inhibitors which incorporate 3-(S)-amino-2-pyrrolidinone as a central template [Ewing et al., Drugs of Future 24 (7):771-787 (1999)]. This compound has a Ki of 7 nM with selectivity >150-fold over thrombin, activated protein C, plasmin and t-PA. It prolongs the PT and .parallel.PTT in a concentration-dependent manner, being more sensitive to the .parallel.PTT. It is a fast binding, reversible and competitive inhibitor of factor Xa.

BX-807834 has a molecular weight of 527 Da and a Ki of 110 .mu.M for factor Xa as compared to 180 .mu.M for TAP and 40 nM for DX-9065a [Baum et al., Circulation. 98 (17), Suppl 1: 179, (1998)].

SEL Series Xa Inhibitors

The SEL series of novel factor Xa inhibitors (SEL-1915, SEL-2219, SEL-2489, SEL-2711: Selectide) are pentapeptides based on L-amino acids produced by combinatorial chemistry. They are highly selective for factor Xa and potency in the pM range. The Ki for SEL 2711, one of the most potent analogues, is 0.003 M for factor Xa and 40 M for thrombin [Ostrem et al., Thromb. Haemost. 73:1306 (1995); Al-Obeidi and Ostrem., Exp. Opin. Ther. Patents 9 (7):931-953 (1999)].

The preservative composition of the present invention may further comprise a short to ultra-short acting broad spectrum anti-microbial agent. Examples of such an agent include, but are not limited to, the agents listed below:

Penicillin—a group of antibiotics produced either by *Penicillium* (natural penicillins) or by adding side chains to the β-lactam ring (semisynthetic penicillins).

Natural penicillins—the first agents of the penicillin family that were produced; ex: penicillins G and V.

Semisynthetic penicillins—modifications of natural penicillins by introducing different side chains that extend the spectrum of antimicrobial activity and avoid microbial resistance.

Monobactam—a synthetic antibiotic with a β-lactam ring that is monocyclic in structure.

Cephalosporin—an antibiotic produced by the fungus Cephalosporium that inhibits the synthesis of gram-positive bacterial cell walls.

Carbapenems—antibiotics that contain a β-lactam antibiotic and cilastatin.

Vancomycin—an antibiotic that inhibits cell wall synthesis.

Isoniazid (INH)—a bacteriostatic agent used to treat tuberculosis.

Ethambutol—a synthetic antimicrobial agent that interferes with the synthesis if RNA.

Aminoglycoside—an antibiotic consisting of amino sugars and an aminocyclitol ring, such as streptomycin.

Tetracycline—a broad-spectrum antibiotic that interferes with protein synthesis.

Chloramphenicol—a broad-spectrum bacteriostatic chemical.

Macrolide—an antibiotic that inhibits protein synthesis, such as erythromycin.

Rifamycin—an antibiotic that inhibits bacterial RNA synthesis.

Quinolone—an antibiotic that inhibits DNA replication by interfering with the enzyme DNA gyrase.

Fluoroquinolone—a synthetic antibacterial agent that inhibits DNA synthesis.

Sulfonamide—a bacteriostatic compound that interferes with folic acid synthesis by competitive inhibition.

Synergism—the principle whereby the effectiveness of two drugs used simultaneously is greater than that of either drug used alone.

Polyene antibiotic—an antimicrobial agent that alters sterols in eucaryotic plasma membranes and contains more than four carbon atoms and at least two double bonds.

Imidazole—an antifungal drug that interferes with sterol synthesis.

Triazole—an antifungal antibiotic used to treat systemic fungal infections.

Griseofulvin—a fungistatic antibiotic.

In another embodiment, the platelet preservation composition can be used in a concentration range from about 0.001 to about 5 mg in any setting that requires the circulation of blood outside the body such as in patients undergoing open heart surgery, renal dialysis, plasmapheresis, and other procedures requiring platelet supplementation.

In another aspect, the present invention relates to a method for extending the shelf-life of platelets using the preservative composition described above. The method comprises admixing the preservative composition of the present invention with inactivated, functional platelets to form preserved platelets with extended shelf-life. The inactivated, functional platelets can be in the form of whole blood, a platelet-containing component of whole blood, or isolated platelets substantially free of red blood cells and other blood nutrients. The preserved platelets can be stored at room temperature, refrigeration temperatures, or freezing temperatures in liquid, frozen, or freeze-dried state to maintain the freshness and function of the platelets.

The preservative composition can be directly added to a blood collection bag, or be kept in a separate bag and combined with the blood after collection. The blood in the collection bag optionally can be treated with an anticoagulant. In a typical setting, the preservative composition is added directly to the blood collection bag.

Typically, the blood is whole blood isolated from a mammal, for use in the same species. In the case of a human, the blood is isolated and separated into the three core components of whole blood, i.e., plasma, cells, and platelets. The whole blood, or only the platelet component of the whole blood, can be treated with the preservative composition. If whole blood is treated, a preferred embodiment contemplates the use of only some components of the proposed preservative composition, such as the antiplatelet agent and anticoagulant, for whole blood storage. The blood can then be fractionated and the platelet component can be further mixed with the preservative composition of the present invention for storage.

If the platelets will be subsequently frozen or freeze dried, the platelets will be mixed with the preservative composition before freezing.

Functional activities of platelets are determined by their ability to aggregate in the presence of certain biological agents and their morphology. Platelet function also can be assessed by the maintenance of the pH upon limited storage of a solution containing the platelets and in vivo haemostatic effectiveness using the rabbit kidney injury model described in Krishnamurti et al., Transfusion, 39:967 (1999). Structural integrity of platelets is assessed by in vivo survival following radiolabeling with carbon-15 or indium-111 and identification of the presence of specific platelet antigens.

The preservative composition of the present invention is used in an amount of about 60 to about 200 ml at room temperature for about one unit of platelets at room temperature, typically about 80 to about 100 ml of platelets. Alternatively, the preservative composition of the present invention is combined with about one unit of whole blood, typically about one pint, and separated into various components to afford about one-sixth to about one-tenth whole blood unit of treated platelets. To achieve the full advantage of the present invention, the preservative composition contains an antiplatelet agent dissolved in about 45 to about 55 ml of an oxygen carrier. When used with an unit of whole blood, the antiplatelet agent can also be dissolved in about 45 to about 55 ml of normal saline to preserve the freshness of the platelets without an oxygen carrier. The selection of an antiplatelet agent and an oxygen miter, and the determination of the amounts for including such components in the preservative composition, are within the capability of, or can be readily determined by, those skilled in the art of preparing preserved platelet compositions.

The platelets used in the invention can be sterilized by chemical sterilization, radiation, or a combination thereof, in the presence of the preferred embodiment. For example, the platelets can be sterilized by chemical filtration; ultraviolet radiation, such as UVA, UVB, and UVC; gamma-radiation; ionizing radiation, such as x-ray radiation; or by using a chemical as a photosensitizer. Methods for sterilizing platelets are well known in the art and include, for example, the methods described in U.S. Pat. Nos. 5,798,238; 5,869,701; 5,955,256; 5,981,163; 6,030,767; 6,087,141; and 6,106,773.

By using the preservative composition of the invention, the platelets can be stored at room temperature. Platelet function also can be better maintained throughout the 5-day storage period mandated by the FDA.

The use of a hemoglobin-based oxygen carrier, even in small volumes, as part of the preservative solution provides significantly greater concentration of oxygen than amounts currently made available by the use of oxygen-permeable storage bags. The combination of platelets with an oxygen carrier (e.g., a stroma-free hemoglobin solution) allows the use of gas impermeable bags, which reduces the high cost associated with using gas permeable bags.

The present invention is further illustrated by the following examples which should not be construed as limiting. The contents of all references, patents and published patent applications cited throughout this application, as well as the Tables are incorporated herein by reference.

The foregoing examples illustrate that an acellular preservative solution for freshly collected platelets can be prepared for improving the functional half-life of platelets. The addition of the preservative solution to freshly collected platelets better maintains the original blood clotting function when infused during the storage period of the platelets. The addition of a preservative solution permits an extended storage of the platelets at refrigeration temperatures, and allows the platelets to maintain blood clotting properties without affecting the half-life of the platelets in circulation once transfused. As a result, the platelets stored for an extended period can be used for transfusions while saving a substantial amount of effort and cost.

EXAMPLE 1

General Procedure of Preparing the Preservative Solution Containing Antiplatelet In 50 ml of an acellular chemically modified hemoglobin-based carrier substantially free of red cell membrane (stroma) contaminants, with a hemoglobin concentration of 12-20 gm/dl and a methemoglobin concentration of less than 5%, the following active ingredients were added:

1) A GPIIb/IIIa inhibitor, such as eptifibatide (INTEGRILIN®, Schering-Plough Corporation, Kenilworth, N.J., U.S.A.), XJ757, DUP728, XR299 or aggrastat (tirofiban) in an amount of 0.001-5.0 mg.

2) An anti-inflammatory drug (NSAID), such as ibuprofen, in an amount of 20-60 mg.

The above preservative solution can be added either to the blood collection bag containing the anticoagulant or to a separately attached bag. If the platelets are going to undergo a sterilizing procedure, chemical or radiation, then the preservative composition is either added prior to sterilization or added in a separately attached bag.

3) A short to ultra-short acting Xa inhibitor such as DX-9065a, BX-80783, RPR-120844 or an Xa inhibitor from the SEL-series or other short acting Xa inhibitor in an amount of 0.001-5 mg.

4) An energy source such as glucose or citrate to sustain aerobic metabolism

5) Electrolytes such as Na, Cl, and Mg.

TABLE 1 provides the concentration ranges for some commonly used energy sources and electrolytes.

TABLE 1

Commonly Used Energy Sources and Electrolytes

| Component | Concentration (mM) |
|---|---|
| NaCl | 80 to 120 |
| KCl | 5 to 15 |
| $MgCl_2/MgSO_4$ | 2 to 5 |
| $Na_2$ Citrate | 5 to 40 |
| $NAH_2PO_4/Na_2HPO_4$ | 5 to 30 |
| Na Acetate | 20 to 40 |
| Na Gluconate | 15 to 30 |
| Glucose | 20 to 50 |
| Maltose | 25 to 35 |
| D-Mannitol | 25 to 40 |

EXAMPLE 2

In Vitro Assessment of Platelet Function and Stability

Cell counts in the platelet concentrates and mean platelet volume were determined electronically using a particle counter. The pH, $pO_2$, $pCO_2$, and bicarbonate levels were determined in a blood gas analyzer. Glucose, lactic acid, and lactic dehydrogenase levels in the platelet concentrates were measured by standard clinical chemistry methodology. Platelet function was measured by aggregometry using ADP and collagen as agonists and by thrombelastography (TEG).

Thrombelastography (TEG)

The principle of TEG is based on the measurement of the physical viscoelastic characteristics of blood clot. Clot formation was monitored at 37° C. in an oscillating plastic cylindrical cuvette ("cup") and a coaxially suspended stationary piston ("pin") with a 1 mm clearance between the surfaces, using a computerized Thrombelastograph (TEG Model 3000, Haemoscope, Skokie, Ill.). The cup oscillates in either direction every 4.5 seconds, with a 1 second mid-cycle stationary period; resulting in a frequency of 0.1 Hz and a maximal shear rate of 0.1 per second. The pin is suspended by a torsion wire that acts as a torque transducer. With clot formation, fibrin fibrils physically link the cup to the pin and the rotation of the cup as affected by the viscoelasticity of the clot (Transmitted to the pin) is displayed on-line using an IBM-compatible personal computer and customized software (Haemoscope Corp., Skokie, Ill.). The torque experienced by the pin (relative to the cup's oscillation) is plotted as a function of time (FIG. 1).

TEG assesses coagulation by measuring various parameters such as the time latency for the initial initiation of the clot (R), the time to initiation of a fixed clot firmness (k) of about 20 mm amplitude, the kinetic of clot development as measured by the angle (.parallel.), and the maximum amplitude of the clot (MA). The parameter A measures the width of the tracing at any point of the MA. Amplitude A in mm is a function of clot strength or elasticity. The amplitude on the TEG tracing is a measure of the rigidity of the clot; the peak strength or the shear elastic modulus attained by the clot, G, is a function of clot rigidity and can be calculated from the maximal amplitude (MA) of the TEG tracing.

The following parameters were measured from the TEG tracing (FIG. 1):

R, the reaction time (gelation time) represents the latent period before the establishment of a 3-dimensional fibrin gel network (with measurable rigidity of about 2 mm amplitude).

Maximum Amplitude (MA, in mm), is the peak rigidity manifested by the clot.

Shear elastic modulus or clot strength (G, dynes/cm2) is defined by: G (5000 A)/(100−A).

Blood clot firmness is important function parameters for in vivo thrombosis and hemostasis because the clot must stand the shear stress at the site of vascular injury. TEG can assess the efficacy of different pharmacological interventions on various factors (coagulation activation, thrombin generation, fibrin formation, platelet activation, platelet-fibrin interaction, and fibrin polymerization) involved in clot formation and retraction.

Blood Sampling

Blood was drawn from consenting volunteers under a protocol approved by the Human Investigations Committee of William Beaumont Hospital. Using the two syringe method, samples were drawn through a 21 gauge butterfly needle and the initial 3 ml blood was discarded. Whole blood (WB) was collected into siliconized Vacutainer tubes (Becton Dickinson, Rutherford, N.J.) containing 3.8% trisodium citrate such that a ratio of citrate whole blood of 1:9 (v/v) was maintained. TEG was performed within 3 hrs of blood collection. Calcium was added back at a final concentration of 1-2.5 mM followed by the addition of the different stimulus. Calcium chloride by itself at the concentration used showed only a minimal effect on clot formation and clot strength.

Statistical Analysis

Data are expressed as mean.+−.SEM. Data were analyzed by either paired or group analysis using Student's t-test or ANOVA when applicable; differences were considered significant at P<0.05 or less.

Figure 2C:
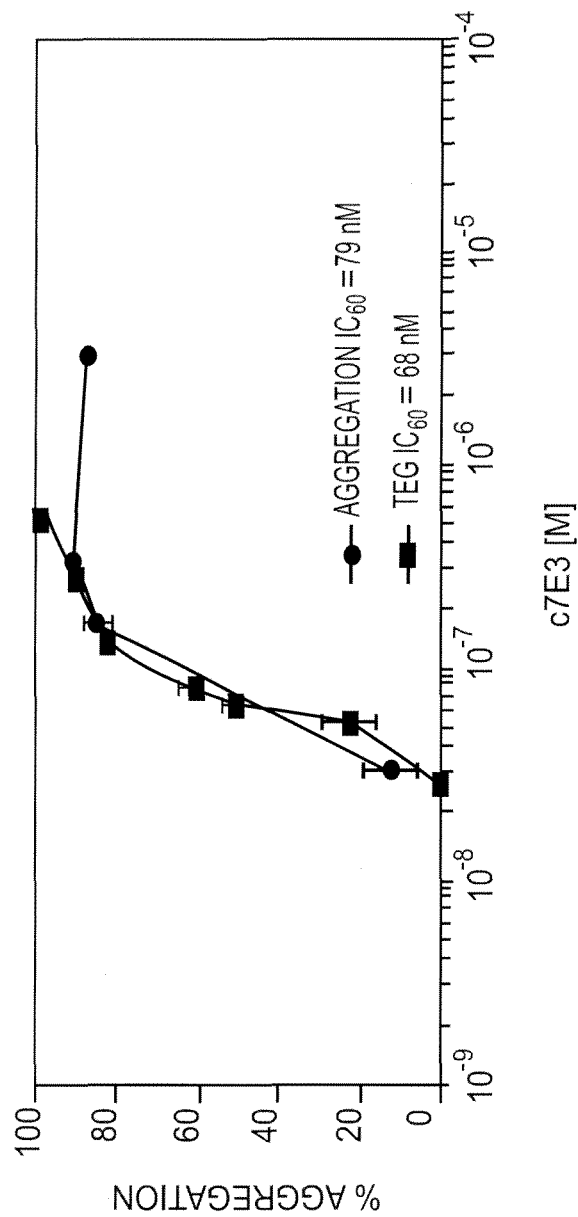
FIG. 2C show comparable effect of c7E3 on platelet aggregation and platelet/fibrin clot.

Effect of GPIIb/IIIa Antagonists c7E3 (Long Acting Versus Short/Ultra Short Acting) on Tissue Factor Mediated Clot Retraction in Human Whole Blood Thrombelastography Increasing concentrations of GPIIb/IIIa antagonists impaired the rate of increase in G force developed without prolonging R by tissue factor (TF)-activated whole blood clots. FIGS. 2A-2C are representative tracings showing efficacy of GPIIb/IIIa antagonist c7E3 in inhibiting TF-mediated clot formation under shear use of TEG.

Determination of Dissociation Rates

To determine platelet/GPIIb/IIIa ligand dissociation rate ($t_{1/2}$), platelet rich plasma samples were treated for 60 minutes with 0.04 μM of $^3$H-Roxifiban or the various Roxifiban isoxazoline analogs including XR299, DMP802, and XV454. Following this 60-minute incubation period, the tubes were centrifuged for 10 minutes (150×g). The resulting $^3$H-radioligand/platelet rich plasma (PRP) complex was carefully removed and centrifuged for an additional 10 minutes (1,500×g). The resulting platelet poor plasma (PPP) was removed and the platelet pellet re-suspended ($1.6×10^8$/ml) in fresh PPP. Five hundred microliters of this suspension was transferred to wells of a 24-well plate (blocked with 5% bovine serum albumine (BSA)). To initiate dissociation, dilution with 1.0 ml Tris buffer, pH 7.4 containing 100 μM non-radiolabeled ligand was added to the wells. At designated time points (0-60 minutes), the $^3$H-GPIIb/IIIa antagonist/PRP complex was removed from the wells. For GPIIb/IIIa antagonists with fast platelet dissociation rate the $t_{1/2}$ (min.) for the dissociation of platelet bound $^3$H-GPIIb/IIIa antagonists was carried out at short intervals. The resulting platelet pellet was counted using a liquid scintillation counter. CPMs recovered are compared to the control (t=0) and presented as percent bound per $0.8×10^8$ platelets over time. The t½ for the platelet dissociation of short to ultra-short acting GP IIb/IIIa antagonists including Integrilin, Tirofiban, XR299, XV454, XV457 ranged from 0.05-0.25 minutes (Table 3). As used herein, the term "short-to-ultra-short" refers to the half life of the compound that is based on (i) in vitro displacement results as shown in Table 3 and is based on (ii) in vivo half life after the infusion of the preserved platelets, which is less than 4 hours in human.

Radiolabel/Platelet Elution Profile

Preparation of Gel Columns and Platelets

About 200 ml of gel slurry (Sepharose-CL4B, #17-0150-01, Pharmacia) was placed in a large buchner funnel and washed with 1 liter of distilled water. The washed gel was reconstitute with water to form a thick slurry. Two columns were prepared by loading about 120 ml of the washed gel slurry to each column (Siliconize column with Sigma-Cote, Sigma Chemical #SL-2; or Bio-Rad Column #737-2531). One column was used to determine platelet counts, while the other was used to determine CPMs. The packed columns were washed with 250 ml of distilled water, followed with 150 ml of HBMT through the gel to allow buffer/gel equilibration.

Human whole blood is collected via venupuncture as described above and placed in intovacutainers containing 0.5 ml of 0.1M buffered sodium citrate (Becton/Dickinson). The whole blood was centrifuged for 10 minutes at 150×g (~1000 rpm Sorvall RT6000). The PRP was collected and kept in a capped polypropylene tube until use.

Radiolabeling and Platelet Elution 3.5 ml of PRP was incubated with either a radiolabeled ligand or a cold ligand for 15 minutes at 22° C. The PRP was then carefully loaded onto a Sepharose gel column and eluted with Hepes Buffered Modified Tyrodes Solution (HBMT, see Table 2)) collect 60, 2 ml fractions (total volume=~120 ml) from each column.

Figure 3:
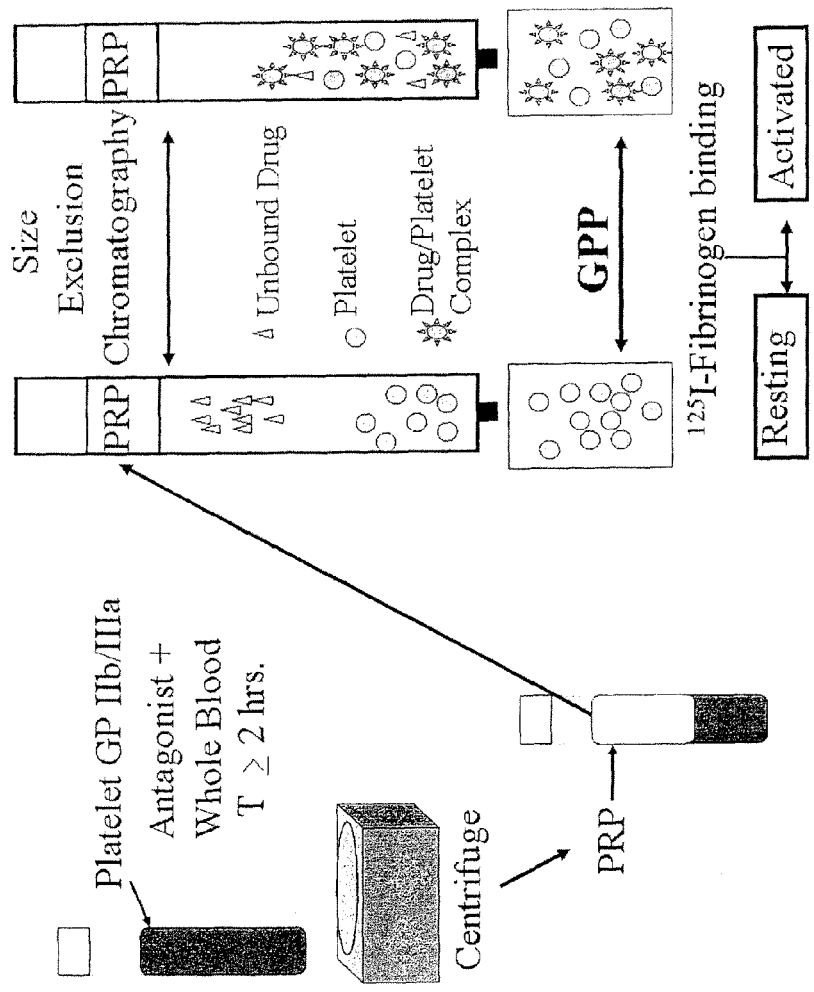
FIG. 3 is a diagram showing a protocol of GP IIb/IIIa antagonists and platelet fibrinogen binding short to ultra-short acting GP IIb/IIIa antagonists including those that are separated from platelet upon size exclusion chromatography.

Non radioactive fractions were counted on a coulter counter (T540), in order to determine platelet counts. 250 µl of the radiolabeled elutions from each fraction were counted on a beta counter (Packard Minaxi Tri-Carb). The labeling/eluting process is summarized in FIG. 3

TABLE 2

Hepes Buffered Modified Tyrodes Solution (HBMT)

| CHEMICAL | [M] | g/l |
|---|---|---|
| NaCl | 0.14 | 8.2 |
| KCl | 0.0027 | 0.201 |
| $NaH_2PO_4 + H_2O$ | 0.0004 | 0.055 |
| $NaHCO_3$ | 0.012 | 1.0 |
| GLUCOSE | 0.0055 | 0.991 |
| BSA fraction-V | 3.5 | |
| HEPES | 0.005 | 1.192 |

NOTE:
pH 7.4 at 22° C.

Table 3 shows dissociation rates of short acting (e.g., XR290) and long acting (e.g., c7E3) GPIIb/IIIa antagonists to human platelets

TABLE 3

| | Long acting | | | Short to ultra-short acting | | | |
|---|---|---|---|---|---|---|---|
| Binding Parameters | XV459 | XV454 | c7E3 | DMP728* | XR290* | Tirofiban* | Integrilin* |
| Dissociation Rates ($t\frac{1}{2}$ - Minutes) | 7.0 | 32.0 | 40.0 | 0.2 | 0.05 | 0.1 | 0.25 |

In vitro $t\frac{1}{2}$ of 0.1 minute translate to 30 minutes washout in vivo in animals or human, $t\frac{1}{2}$ of 7 minutes translate into 20-24 hours washout in vivo in animals or human, and $t\frac{1}{2}$ of 30-40 minutes translate to washout of 7-10 days (the life time of the platelet in the circulation).

*For platelet preservation, a short to ultra-short GPIIb/IIIa antagonists will be the preferred ones.

EXAMPLE 3

In Vivo Assessment of Platelet Function and Stability

EXAMPLE 3(a)

Circulation Half-Life

The platelets stored in the preservative solution were radioactively labeled by C15 or In111. The labeled platelets were injected into rabbits via the ear vein. Blood samples were drawn at different time points and the radioactively measured. The radioactive decay curve provided an estimate of the circulating half-life of the platelets. The resulting decay curve was compared with traditionally stored platelets that were labeled in a similar manner.

EXAMPLE 3(b)

In Vivo Bleeding Model

A rabbit model was made thrombocytopenic (platelet counts approximately 30,000 per *L or 10% of normal) by subcutaneous injections of busulfan (25 mg/kg). Two weeks following busulfan treatment, the rabbits were treated by the surgery procedures described by Krishnamurti et al, Transfusion, 39:967 (1999). Blood samples were obtained at different time points and the survival of the platelets determined. These values were compared to that obtained by traditionally stored platelets.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the claimed components and steps in any sequence which is effective to meet the objectives there intended, unless the context specifically indicates the contrary

What is claimed is:

1. A platelet preservation package, comprising: a platelet preservation composition comprising:
 a short-to-ultrashort acting antiplatelet agent, wherein said antiplatelet agent is a GPIIb/IIIa inhibitor;
 a short-to-ultrashort acting anticoagulant, wherein said anticoagulant is a compound that reversibly inhibits factor Xa, or factor IIa, or both; and
 a bag for storing the platelet preservation composition,
 wherein said antiplatelet agent and said anticoagulant are stored in said bag and wherein said composition is capable of extending the shelf-life of platelets when mixed with said platelets in said bag.

2. The platelet preservation package of claim 1, wherein said antiplatelet agent is capable of reversibly blocking platelet activation and/or aggregation by blocking sites on the platelet surface.

3. The platelet preservation package of claim 1, wherein said antiplatelet agent is selected from the group consisting of eptifibatide, orbofiban, xemilofiban, lamifiban, tirofiban, and mixtures thereof.

4. The platelet preservation package of claim 1, wherein said antiplatelet agent is selected from the group consisting of linear and cyclic RGD-containing peptides.

5. The platelet preservation package of claim 4, wherein said linear and cyclic RGD-containing peptides are conjugated to a nitric oxide donor.

6. The platelet preservation package of claim 1, wherein said antiplatelet agent is a pharmaceutically acceptable antiplatelet agent and has a circulating half-life of inhibition of about less than 4 hours.

7. The platelet preservation package of claim 1, wherein said antiplatelet agent comprises about 0.001 mg to about 5 mg of a GPIIb/IIIa inhibitor.

8. The platelet preservation package of claim 1, wherein said anticoagulant is a short-to-ultrashort acting Xa inhibitor with a circulating half-life of less than 4 hours.

9. The platelet preservation package of claim 1, wherein said anticoagulant is a short-to-ultrashort acting IIa inhibitor, and wherein said short-to-ultrashort acting IIa inhibitor is selected from the group consisting of hirudin, hirulog, melgatran, and combinations thereof.

10. The platelet preservation package of claim 1, wherein said anticoagulant is a pharmaceutically acceptable anticoagulant and is a combination of at least one short-to-ultrashort acting IIa inhibitor, and at least one short-to-ultrashort acting Xa inhibitor.

11. The platelet preservation package of claim 1, wherein the preserved platelet composition further comprises a short-to-ultrashort acting broad spectrum anti-microbial agent selected from the group consisting of: natural penicillins, semisynthetic penicillins, monobactam, cephalosporin, carbapenems, vancomycin, isoniazid, ethambutol, aminoglycoside, tetracycline, chloramphenicol, macrolide, rifamycin, quinolone, fluoroquinolone, sulfonamide, polyene antibiotic, imidazole, triazole, griseofulvin and combinations thereof.

12. A platelet preservation package, comprising: a platelet preservation composition comprising:
  a short-to-ultrashort acting antiplatelet agent, wherein said antiplatelet agent is a GPIIb/IIIa inhibitor;
  a short-to-ultrashort acting anticoagulant, wherein said anticoagulant is a compound that reversibly inhibits factor Xa; and
  a blood collection bag,
  wherein said antiplatelet agent and said anticoagulant are stored in said blood collection bag and wherein said composition is capable of extending the shelf-life of platelets when mixed with said platelets in said blood collection bag.

13. A platelet preservation package, comprising: a platelet preservation composition comprising:
  a short-to-ultrashort acting antiplatelet agent, wherein said antiplatelet agent is a GPIIb/IIIa inhibitor;
  a short-to-ultrashort acting anticoagulant, wherein said anticoagulant is a compound that reversibly inhibits factor IIa; and
  a blood collection bag,
  wherein said antiplatelet agent and said anticoagulant are stored in said blood collection bag and wherein said composition is capable of extending the shelf-life of platelets when mixed with said platelets in said blood collection bag.

* * * * *